United States Patent [19]

Kim

[11] Patent Number: 5,108,748
[45] Date of Patent: Apr. 28, 1992

[54] METHOD OF TREATMENT DURING WITHDRAWAL FROM ALCOHOL DEPENDENCY

[76] Inventor: Tuk M. Kim, 673 Southgate Ave., Daly City, Calif. 94015

[21] Appl. No.: 510,741

[22] Filed: Apr. 18, 1990

[51] Int. Cl.⁵ ............................................. A61K 35/78
[52] U.S. Cl. ................................................. 424/195.1
[58] Field of Search ..................... 424/195.1; 514/810, 514/811, 812, 648

[56] References Cited

U.S. PATENT DOCUMENTS

| | | | |
|---|---|---|---|
| 4,569,843 | 2/1986 | Kim | 424/195.1 |
| 4,696,818 | 9/1987 | Kim | 424/195.1 |

FOREIGN PATENT DOCUMENTS

WO/03551 10/1982 PCT Int'l Appl. ................. 514/811

Primary Examiner—Johnnie R. Brown
Assistant Examiner—Anita Varma
Attorney, Agent, or Firm—Flehr, Hohbach, Test, Albritton & Herbert

[57] ABSTRACT

A method is provided for treatment of methadone and/or alcohol dependent subjects comprising the step of orally administering to such subjects during the period of drug withdrawal an herbal composition comprising *Radix angelica sinesis, Herba pogostemi, Cyperus rotundus* and *Squama manitis pentadactylae*.

6 Claims, No Drawings

METHOD OF TREATMENT DURING WITHDRAWAL FROM ALCOHOL DEPENDENCY

The present invention is directed to a method for treating persons during withdrawal from methadone and/or alcohol dependency. In particular, the present invention is directed to method of treatment during withdrawal from this dependency comprising orally administering an herbal composition.

During the period of withdrawal from methadone and/or alcohol dependency, a dependent subject will normally experience withdrawal symptoms. The symptoms may include physical manifestations due to the body's elimination process of the toxic products accumulated in the blood, internal passages, and organs. The physical withdrawal symptoms may include tearing, discharges of bronchial mucous, excessive perspiration, diarrhea, vomiting, dark urine and spasmodic attacks. Other withdrawal symptoms result from the effect of the alcohol or methadone on the nervous system which is usually depressed and weakened. These symptoms include irritability, anxiety, depression, headaches and various pains throughout the body. These withdrawal symptoms are not an indication of disease but rather an indication that the body is restoring itself to a healthy state.

The symptoms are therefore a part of the natural effect of the self-healing capabilities of the body through the elimination of toxic waste products.

It is, therefore, an object of the present invention to provide a method of treatment of persons undergoing methadone and/or alcohol dependency withdrawal to alleviate, and in some cases, eliminate the unpleasantness accompanying the withdrawal.

It is a further object of the invention to assist natural processes of detoxification and elimination of toxic products from the blood and body, and provide fresh new elements required by the body.

According to the present invention a method is provided for alleviating the unpleasantness of withdrawal by administering to the subject periodic unit doses of an herbal composition comprising the following four components: *Radix angelica sinensis, Herba pogostemi, Cyperus rotundus* and *Squama manitis pentadactylae*. The herb *Pogostemon cablin* may be alternatively used in place of the *Herba pogostemi*. The first three of these herbs are commercially available and are indigenous to Asia. The last herb is also commercially available and is an epidermal scale from wild animals (i.e. scale of manis pendadactila; ref. Chinese Herbal Dictionary, No. 3549, page 1727, edited 1977, Shanghai). Preferably, the herbs will be formulated into unit dosage forms so that the unit doses may be administered periodically during the period of withdrawal. While the relative proportions of the herbs in each unit dose is not critical, it is preferred that each of the *Radix angelica sinensis, Herba pogostemi* and *Cyperus rotundus* be utilized in approximately equal proportions and that the amount of *Squama manitis pentadactylae* be utilized in a greater proportion than any other single herbal ingredient. Preferably, 1 to 5 parts by weight each of the *Radix angelica sinensis, Herba pogostemi* and *Cyperus rotundus* may be utilized with 2 to 10 parts by weight of the *Squama manitis pentadactylae*.

Most preferred is a proportion of *Radix angelica sinensis:pogostemi:Cyperus rotundus:Squama manitis pentadactylae* of 1:1:1:3.

Preferably, each ingredient should be separately triturated, as for example, by mortar and pestle, until they are reduced to a fine powder. In its natural state, *Cyperus rotundus* is characterized by a fuzzy exterior and this fuzz should be eliminated first by roasting then by trituration whereby the fuzz will be easily pulverized. Before trituration, the *Squama manitis pentadactylae* must be roasted with sand to a golden color.

The composition is to be administered orally and preferably should be prepared in unit dosage forms. A unit dosage will comprise from 3 to about 10 grams per dose, preferably, about 7 grams per dose. The composition may be administered in the form of a powder, capsule, solution, tablet, and the like. The composition may be formed into conventional tablets and capsules utilizing pharmaceutically acceptable inert carriers such as lactose, glucose, gelatin, and the like. Preferably, the composition may be mixed with lactose or other sweetening agent since the sweet taste is soothing to the stomach.

The frequency of treatment will depend upon the individual subject, the degree of methadone and/or alcohol dependency, body weight and the general state of health. Typically, for the first four days of withdrawal treatment, about 10 dosage units (7 gram per unit dose) may be administered per day, at intervals of about 2 to 2½ hours. During the next four days, approximately six doses may be administered per day at intervals of 4 hours. After this, three doses per day may be administered, one dose every 8 hours for several days according to the condition of the subject.

It has surprisingly been found that during the period of treatment when utilizing the composition according to the present invention, the withdrawal pain is substantially decreased at a rapid rate and, furthermore, the compositions according to the present invention appear to cause a violent physical reaction in the subject if an addictive drug such as morphine or methadone is taken during the withdrawal period. For example, when being treated with the composition according to the present invention, an injection of morphine may cause a patient to become sick with fever and pain, thereby greatly reducing the tendency of the subject to return to drug dependency.

The herbs according to the present invention have the following characteristics. *Radix angelica sinensis* is spicy sweet with a warm and bitter aftertaste. According to traditional herbal pharmacology this herb is believed to vitalize and balance the blood by eliminating toxic elements, assist in the metabolism and secretion of hormones, and to have a slight tranquilizing and pain relieving effect. *Herba pogostemi* is spicy to taste with a warm aftertaste and is believed to promote elimination of waste products being helpful in relieving vomiting, diarrhea and relieving headaches and abdominal pain. Cyperus rotundus is spicy, bitter-sweet and neutral and is believed to assist in blood circulation and suppressing headache and stomach cramps. *Squama manitis pentadactylae* is salty and slightly toxic unless heated to a golden color before use. It is believed to assist in excretion and secretion, as well as relieving pain and soothing the nervous system.

Having described the specific embodiments of the present invention, the following are examples. However, the following examples are intended to be illustrative of the invention and the invention is not intended to be limited thereby.

EXAMPLE 1

A fifty-two year old male previously addicted to heroin but on methadone maintenance (70 mg/day for 7 months) and still alcohol dependent is treated according to the present invention using a unit dosage form of 7 grams containing *Radix angelica sinensis, Herba pogostemi. Cyperus rotundus* and *Squama manitis pentadactylae* in proportions of 1:1:1:3. The subject is treated for six days using 2 (about 15 g.) tablespoon doses orally administered every 2½ during waking hours. The subject experiences no serious pain and subsequent to the treatment, dependence on methadone and alcohol use is discontinued. The subject previously had been an heroin addict for about 35 years and was alcohol dependent.

EXAMPLE 2

A forty-nine year old male initially taking methadone (70 mg/day) was treated for four days according to the treatment described above in Example 1. The subject previously had an addiction to heroin and was alcohol dependent. Just prior to treatment, methadone intake was ceased, and heroin use had been taken up for one week (3 times daily). During treatment (12 days), the subject experienced decreasing pain, and improved ability to sleep.

EXAMPLE 3

A thirty-nine year old male having an addiction to heroin was on methadone maintenance (33 mg/day), and used alcohol excessively (4 qts. wine per day). After 3 weeks of treatment according to Example 1, accompanied by acupressure about every 2-3 days, pain and other symptoms of addition dissipated.

EXAMPLE 4

A subject is on 33 mg/day of methadone. The subject drank approximately 1 quart or more of wine/day for a year prior to treatment. The subject suffered from headaches, lack of sleep, and body aches. After taking 1 to 2 tablespoons of the herbal composition in Example 1 approximately every 2 hours (waking hours) for 4 days, pain dissipated significantly and insomnia was no longer a problem.

What is claimed is:

1. A method for treatment of alcohol dependent subjects comprising the step of orally administering during the period of alcohol withdrawal a composition comprising *Radix angelica sinensis. Herba pogostemi, Cyperus rotundus* and *Squama manitis pentadactylae* in unit dosage form.

2. A method according to claim 1 wherein said unit dosage comprises the components in proportion of 1-5 parts each of *Radix angelica sinensis, Herba pogostemi, Cyperus rotundus* and 2-10 parts of *Squama manitis pentadactylae.*

3. A method according to claim 2 wherein said unit dosage comprises a total of 3 to 10 grams.

4. A method according to claim 3 wherein said unit dosage comprises 7 grams.

5. A method according to claim 4 wherein said unit dosage is administered in intervals from 2 to 8 hours per day.

6. A method according to claim 3 wherein said properties are 1 part each of *Radix angelica sinensis, Herba pogostemi* and *Cyperus rotundus* and 3 parts of *Squama manitis pentadactylae.*

* * * * *